(12) United States Patent
Kwon et al.

(10) Patent No.: US 7,998,937 B2
(45) Date of Patent: Aug. 16, 2011

(54) FLAVONOID COMPOUND HAVING AN ANTIVIRAL ACTIVITY

(75) Inventors: Dur Han Kwon, Daejeon (KR); Wha Jeong Choi, Daejeon (KR); Choong Hwan Lee, Daejeon (KR); Jin Hee Kim, Daejeon (KR); Man Bae Kim, Jinju-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 369 days.

(21) Appl. No.: 12/096,977

(22) PCT Filed: Nov. 3, 2006

(86) PCT No.: PCT/KR2006/004566
§ 371 (c)(1),
(2), (4) Date: Aug. 26, 2008

(87) PCT Pub. No.: WO2007/069823
PCT Pub. Date: Jun. 21, 2007

(65) Prior Publication Data
US 2009/0171074 A1    Jul. 2, 2009

(30) Foreign Application Priority Data

Dec. 13, 2005   (KR) ................ 10-2005-0122246

(51) Int. Cl.
*A01N 43/04* (2006.01)
*A61K 31/70* (2006.01)
(52) U.S. Cl. ................ 514/27; 514/33; 536/8; 536/18.5; 536/127
(58) Field of Classification Search ................ None
See application file for complete search history.

(56) References Cited

U.S. PATENT DOCUMENTS
6,485,759 B2 *  11/2002  Chantara et al. ............. 424/756

OTHER PUBLICATIONS

Fico et al. RAPD Analysis and flavonoid composition of *Aconitum* as an aid for taxonomic discrimination, Biochemical Systematics and Ecology, 2003, 31(3), 293-301.*

* cited by examiner

*Primary Examiner* — Traviss C McIntosh, III
(74) *Attorney, Agent, or Firm* — Frommer Lawrence & Haug LLP; Ronald R Santucci

(57) ABSTRACT

The present invention relates to a flavonoid compound having an antiviral activity, more particularly to a flavonoid compound obtained by extracting *Houttuynia cordata* with methanol and separating/purifying with chromatography, a method for efficient extraction and purification of the same and an antiviral composition comprising the compound as an active ingredient.

8 Claims, 5 Drawing Sheets

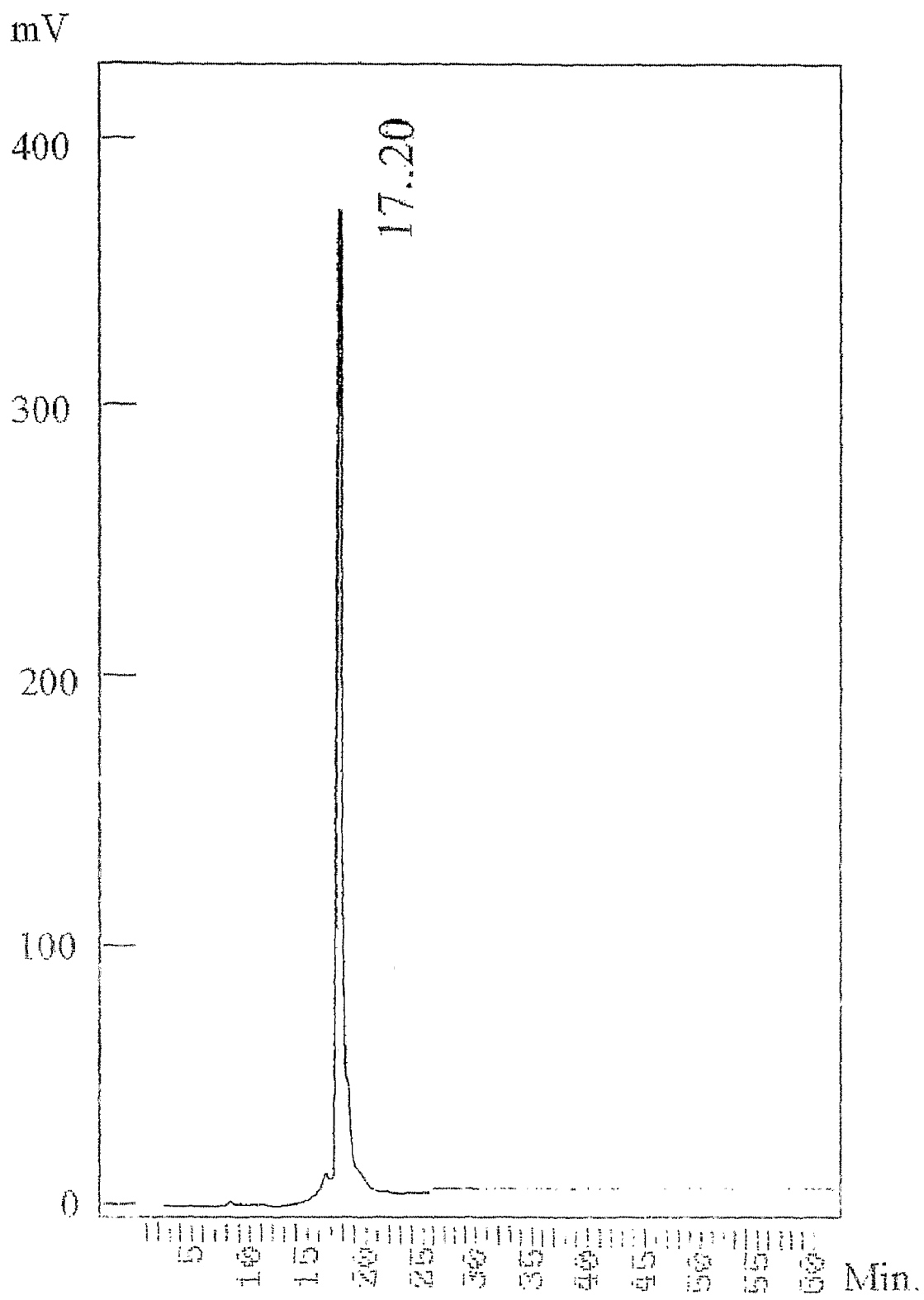
[Fig. 1]

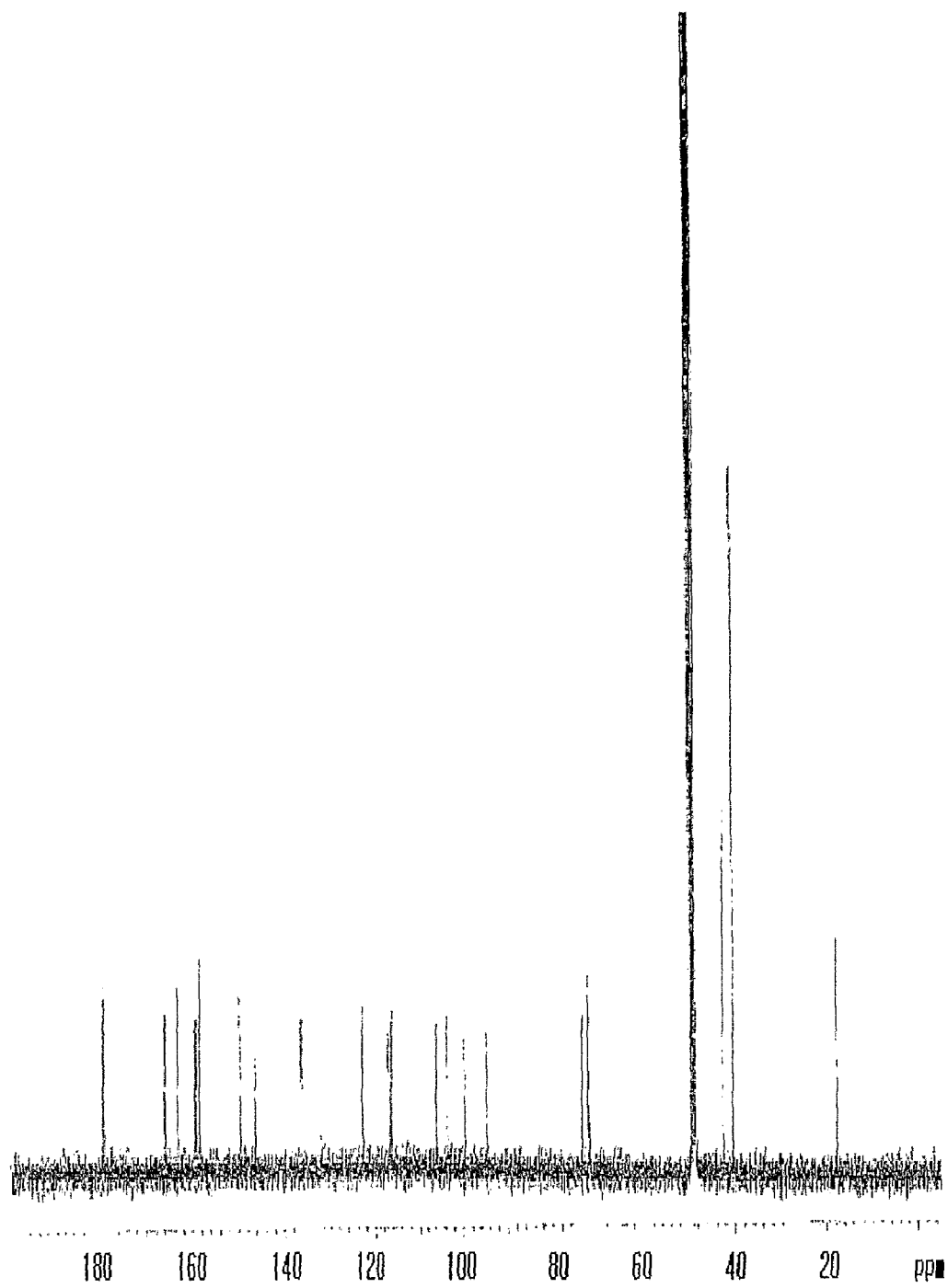
[Fig. 2]

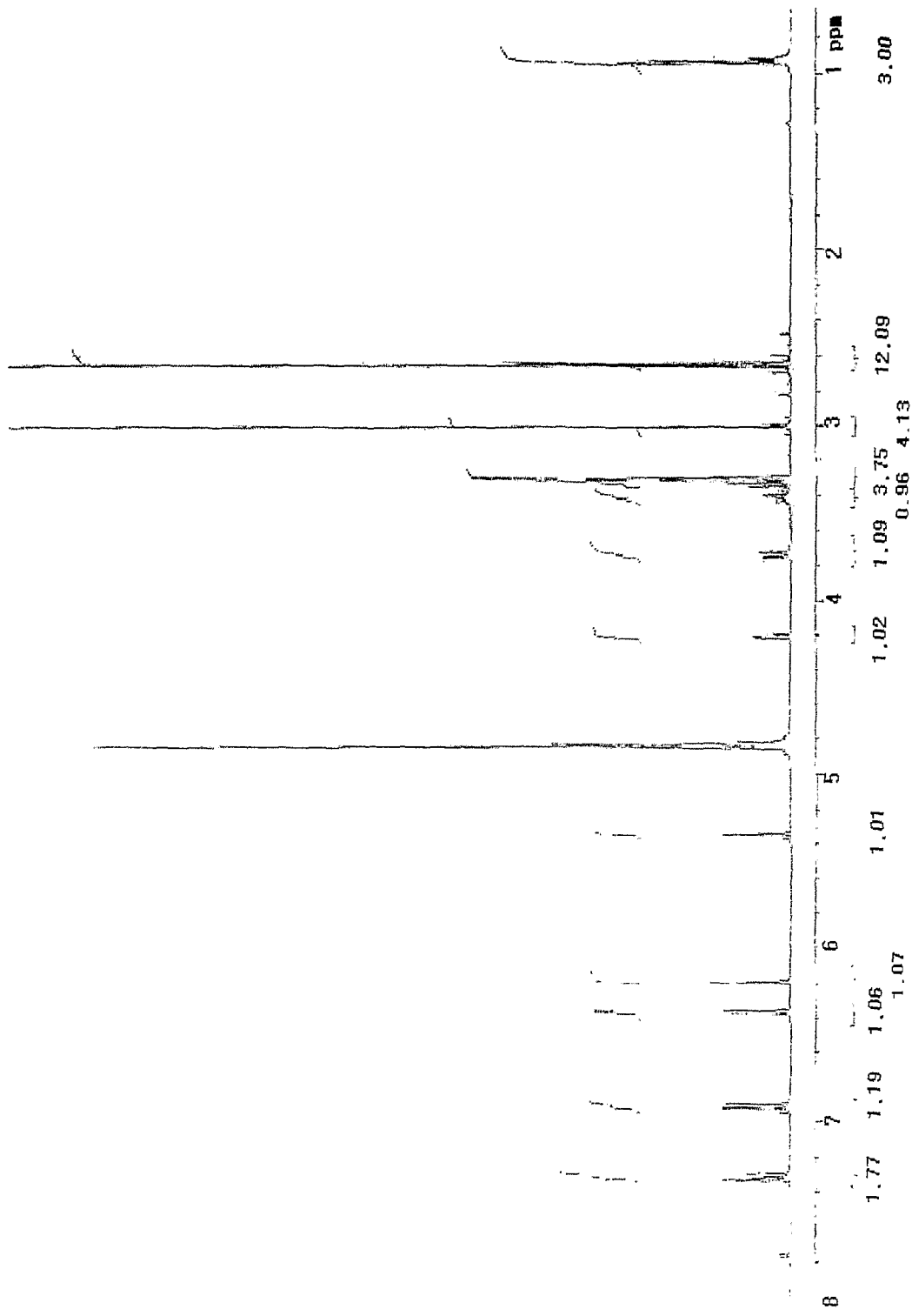
[Fig. 3]

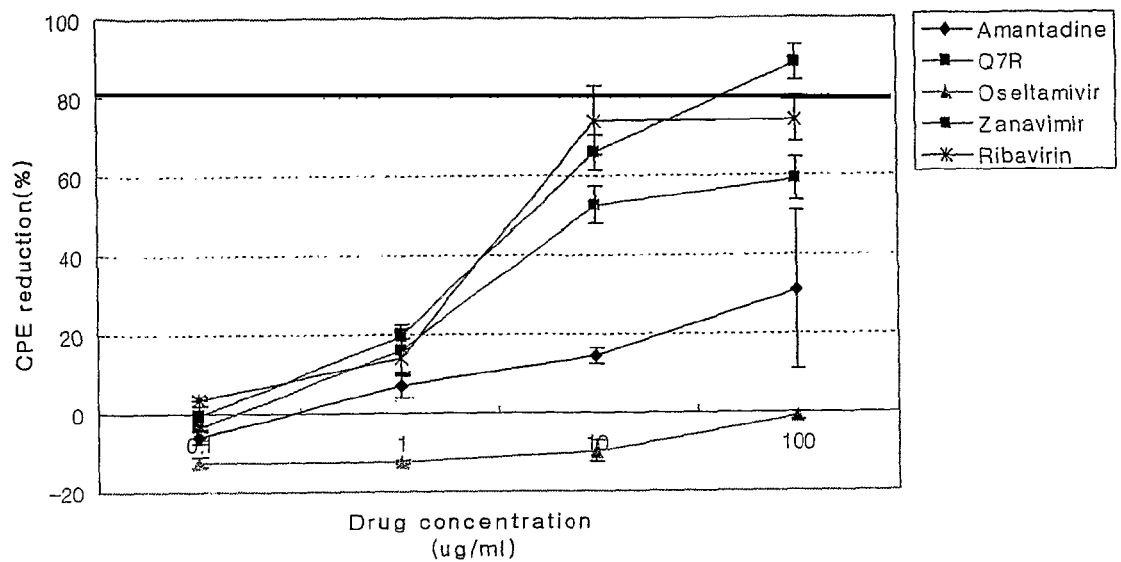
[Fig. 4]
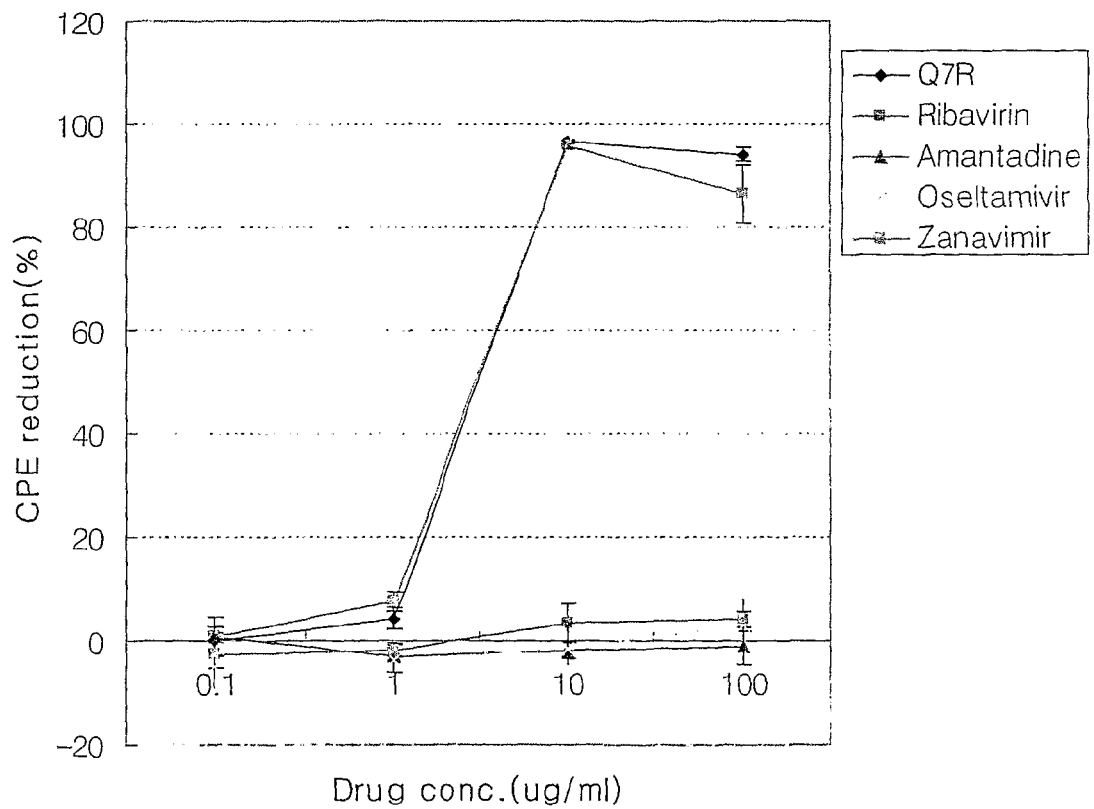
[Fig. 5]

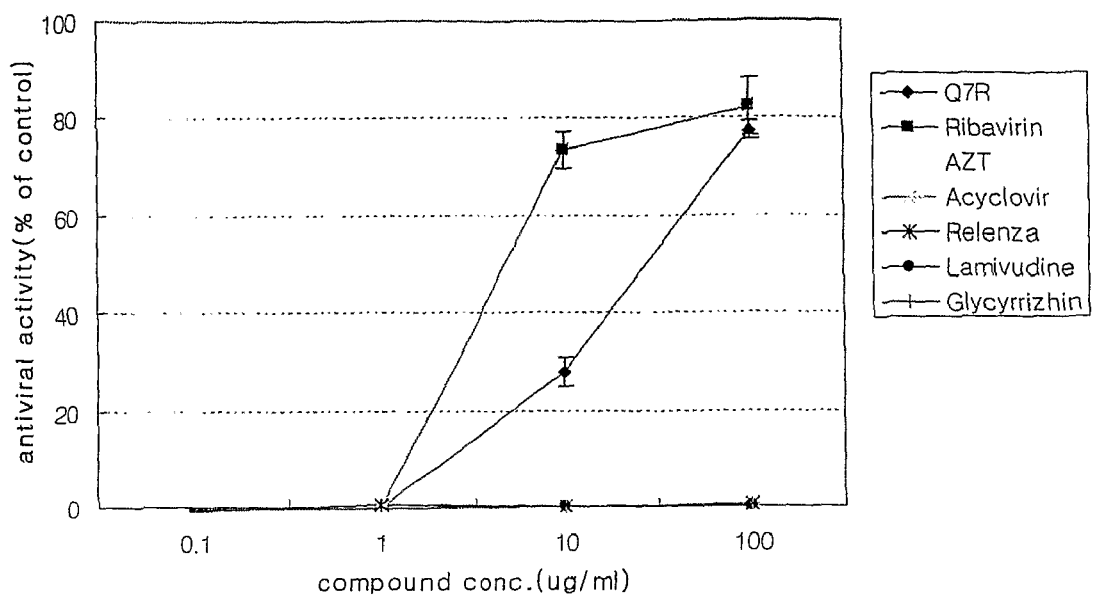
[Fig. 6]
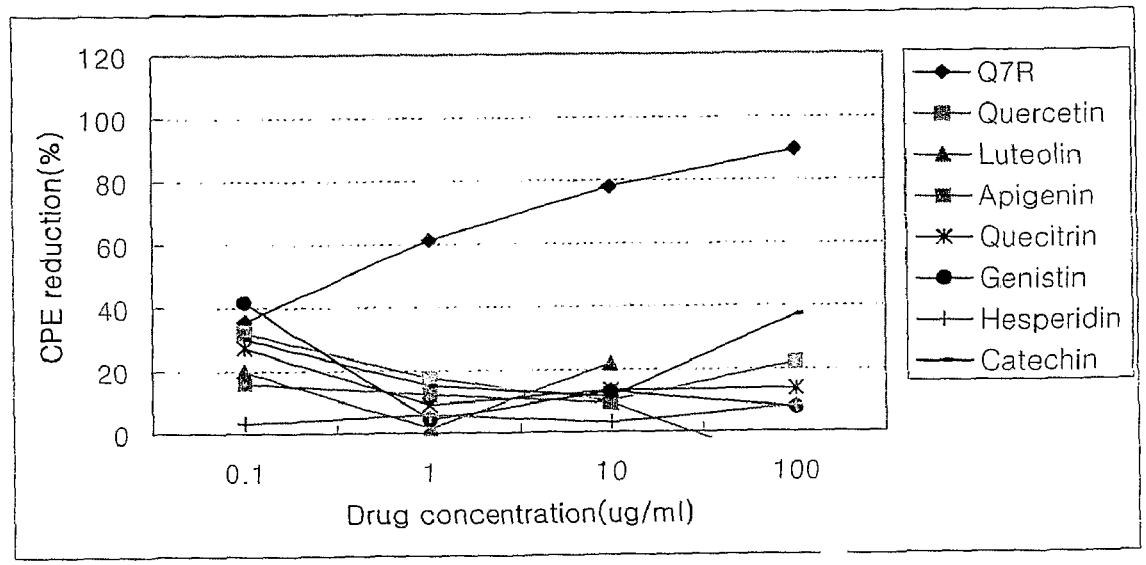
[Fig. 7]

FLAVONOID COMPOUND HAVING AN ANTIVIRAL ACTIVITY

This application is a 371 of PCT/KR2006/004566 filed on Nov. 3, 2006, published on Jun. 28, 2007 under publication number WO 2007/069823 A1 which claims priority benefits from South Korean Patent Application Number 10-2005-0122246 filed Dec. 13, 2005, the disclosure of which is hereby incorporated by reference.

TECHNICAL FIELD

The present invention relates to a flavonoid compound having an antiviral activity, more particularly to a flavonoid compound isolated from *Houttuynia cordata* by extracting with methanol and separating/purifying with chromatography, a method for efficient extraction and purification of the same and an antiviral composition comprising the compound as an active ingredient.

BACKGROUND ART

To date, there has been no report on the pharmacological, biological activities of quercetin-7-rhamnoside. However, the pharmacological activities of the flavonoids or glycosylated flavonoids having similar structures of the quercetin-7-rhamnoside have been widely known [*Journal of Antimicrobial Chemotherapy*, L. C. Chiang, W. Chiang, M. C. Liu and C. C. Lin, Vol. 52(pp 194~198), 2003]. Although there are reports that flavonoids have an antiviral activity against herpesvirus, adenovirus, etc. and that such biflavonoid compounds as robustaflavone have an inhibitory activity against influenza virus, etc. [*Planta Medica*, Yuh-Meei Lin, Vol. 65(pp 120~125)], these antiviral activities do not appear to be excellent.

The present inventors have already shown that the *Houttuynia cordata* extract has antiviral activity against coronavirus [Korean Patent Application No. 2004-97587] and succeeded in isolating the active ingredient from the *Houttuynia cordata* extract, which was identified as quercetin-7-rhamnoside. Korean Patent Application No. 2004-97587 filed by the present inventors discloses the antiviral activity of the *Houttuynia cordata* extract against coronavirus. But, they completed the present invention by confirming that the quercetin-7-rhamnoside has an antiviral activity against coronavirus 700 times superior to that of the *Houttuynia cordata* methanol extract, as well as superior antiviral activity against influenza virus.

Thus, an object of the present invention is to provide an antiviral composition comprising quercetin-7-rhamnoside, a derivative thereof or a pharmaceutically acceptable salt thereof as an active ingredient.

Another object of the present invention is to provide a method for isolating quercetin-7-rhamnoside from the *Houttuynia cordata* extract.

DISCLOSURE

The present invention relates to an antiviral composition comprising a flavonoid compound represented by the formula (1) or a pharmaceutically acceptable salt thereof as an active ingredient:

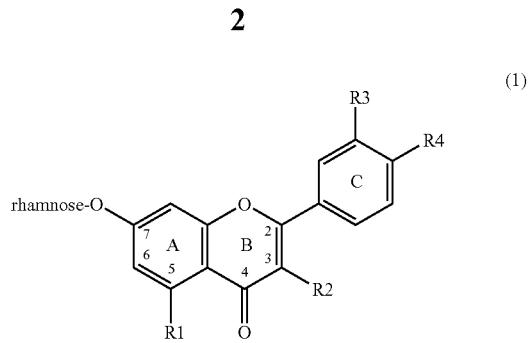

(1)

wherein each of R1, R2, R3 and R4 is selected from H, OH or alkyl.

The present invention also relates to a method for extracting and isolating a compound having an antiviral activity from *Houttuynia cordata*, comprising:

1) extracting *Houttuynia cordata* with methanol, concentrating the extract under reduced pressure and extracting the same with ethyl acetate to obtain an ethyl acetate extract;

2) dissolving the concentrate in methanol and collecting the active fraction with chromatography; and 3) separating the active fraction with chromatography, removing the solvent using a vacuum dryer and freeze-drying the product to obtain a compound having an antiviral activity.

Hereunder is given a more detailed description of the present invention.

The present invention relates to a flavonoid compound obtained by extracting *Houttuynia cordata* with methanol and separating/purifying with chromatography, a method for efficient extraction and purification of the same and an antiviral composition comprising the compound as an active ingredient.

The compound of the present invention may be either synthesized by organic synthesis or extracted and isolated from *Houttuynia cordata* in accordance with the present invention.

The method for extracting the antivirally active compound from *Houttuynia cordata* is as follows.

*Houttuynia cordata* is collected and extracted under reflux using methanol for 24-72 hours. The extract is filtered under reduced pressure and extracted with ethyl acetate.

Silica gel column adsorption chromatography is performed for the concentrated ethyl acetate extract using chloroform/methanol (100/0→0/100) as an eluent to concentrate the active fraction.

The concentrated active fraction is dissolved in methanol and high pressure liquid chromatography (HPLC) is performed using a Sephadex LH-20 column and a water-acetonitrile (25% acetonitrile, 17 minutes) eluent to obtain quercetin-7-rhamnoside.

Through ESI-MS (electron spray ionization mass spectrometer), NMR analysis, etc., the compound represented by the formula I has been confirmed to have the following physicochemical properties:

i) Physical form: powder ii) Molecular weight: 448 iii) Molecular formula: $C_{21}H_{20}O_{11}$ iv) Mass analysis $(M-H)^-$: 448 (m/z)

H-NMR using a deuteromethanol solvent and C-NMR analyses have confirmed the following structure represented by the formula (Ia):

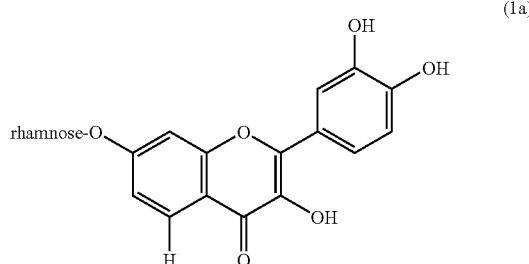
(1a)

The antivirally active compound of the present invention can be used in the form of a pharmaceutically acceptable salt. An acid adduct obtained from a pharmaceutically acceptable free acid is preferred. The compound represented by the above formula Ia can be prepared into a pharmaceutically acceptable acid adduct by the techniques commonly used in the aforementioned technical field. The free acid may be an organic or inorganic acid. Examples of an appropriate inorganic acid are hydrochloric acid, bromic acid, sulfuric acid, phosphoric acid, etc. and examples of an appropriate organic acid are citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, aspartic acid, etc.

The present invention is further relates to an antiviral composition comprising compound represented by the formula (1) or a pharmaceutically acceptable salt thereof as an active ingredient.

Since the pharmaceutical composition comprises the compound represented by the formula (1) or a pharmaceutically acceptable salt thereof as an active ingredient, it inhibits the proliferation of coronaviruses and can be utilized to treat or prevent diarrhea, dehydration, etc. caused by coronavirus infection. Also, since the composition inhibits the proliferation of influenza viruses, it can be utilized to treat or prevent flu or cold or infection by other RNA viruses.

The pharmaceutical composition of the present invention can be administered orally or non-orally, e.g., intravenously, subcutaneously, intraperitoneally or locally, for clinical purposes. Also, it can be utilized in the form of medicines or health foods.

Exemplary oral administration forms of the pharmaceutical composition of the present invention include tablets, troches, lozenges, aqueous or oily suspensions, crude powders or granules, emulsions, hard or soft capsules, syrups or elixirs. For preparation into the form of tablets, capsules, etc., a binder such as lactose, saccharose, sorbitol, mannitol, starch, amylopectin, cellulose or gelatin; an excipient such as dicalcium phosphate; a disintegrator such as cornstarch or sweet potato starch; and a lubricant such as magnesium stearate, calcium stearate, sodium stearyl fumarate or polyethylene glycol wax are contained. For preparation into the form of capsules, a liquid vehicle such as fatty oil is further contained.

The pharmaceutical composition of the present invention can be administered non-orally by subcutaneous injection, intravenous injection, intramuscular injection or intrathoracic injection. For preparation into the non-oral administration form, the compound represented by the formula (1) is mixed with a stabilizer or a buffer in water to obtain a solution or suspension, which is contained in ampules or vials.

In general, the effective dosage of the compound represented by the formula (1) for adults is 1-100 mg/kg per day, preferably 5-20 mg/kg per day. Following the instructions by a doctor or a pharmacist, the compound may be administered several times a day at appropriate time intervals, preferably 2-3 times a day.

The 'health food' as used herein means the food prepared by adding the compound represented by the formula (1) or a pharmaceutically acceptable salt thereof in such foods as beverages, teas, flavors, gums, cookies, etc. or making it into the foods in the form of capsules, powders, suspensions, etc. When taken, the health foods provide specific health-related effects, but they are advantageous over medicines in that they do not cause side effects although taken for a long period time.

DESCRIPTION OF DRAWINGS

FIG. 1 shows the HPLC analysis result of the active fraction isolated from the *Houttuynia cordata* methanol extract.

FIG. 2 shows the $^{13}$C-NMR spectrum of quercetin-7-rhamnoside.

FIG. 3 shows the $^{1}$H-NMR spectrum of quercetin-7-rhamnoside.

FIG. 4 is a graph showing the antiviral activity of quercetin-7-rhamnoside against influenza type A (H1N1/WS/33) virus.

FIG. 5 is a graph showing the antiviral activity of quercetin-7-rhamnoside against influenza type B (B/Lee/40) virus.

FIG. 6 is a graph showing the antiviral activity of quercetin-7-rhamnoside against rotavirus (OSU).

FIG. 7 is a graph showing the antiviral activity of quercetin-7-rhamnoside against rhinovirus 2.

MODE FOR INVENTION

The present invention is illustrated by the following examples, but it should be construed as not limiting the scope of the present invention.

EXAMPLE 1

Isolation and Purification of the Compound Having Anti-coronavirus Activity

In order to obtain a compound capable of inhibiting coronavirus, the present inventors isolated and purified *Houttuynia cordata* by extraction and chromatography.

1 kg of *Houttuynia cordata* obtained from K yeungnam Agricultural Development & Technology Center was extracted with 100% methanol for 48 hours. The extract was concentrated under reduced pressure and extracted with ethyl acetate. The ethyl acetate layer was concentrated and the concentrate was dissolved in 2 mL of methanol. Silica gel column adsorption chromatography was performed using chloroform/methanol (100/0→0/100) as an eluent to concentrate the active fraction. The concentrated active fraction was dissolved in methanol and HPLC was performed using a Sephadex LH-20 column and a water-acetonitrile (25% acetonitrile) eluent (column: C18, flow rate: 1.5 mL/min, detected @ 220 nm). The active fraction at around 17 minutes was isolated [FIG. 1] and the solvent was removed using a vacuum dryer. The residue was freeze-dried to obtain 3.7 mg of the compound represented by the following formula 1a:

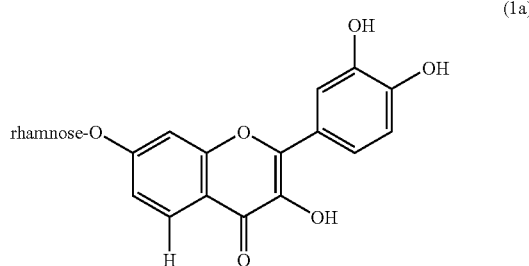

(1a)

EXAMPLE 2

Physicochemical Properties of the Active Compound

ESI-MS (electrospray ionization mass spectrometry, Fisons VG Quattro 400 mass spectrometer, USA) and H- and C-NMR spectroscopy were used to analyze the physicochemical properties of the active compound. NMR spectroscopy was performed using a 5 mm NMR tube after dissolving each test sample with a deuteromethanol solvent. Chemical shift was measured using each solvent as internal standard or based on the peak of TMS (tetramethylsilane). Physical form, molecular weight, molecular formula and mass were analyzed for the compound.

The active compound was in the form of powder. Molecular weight was 448 and the molecular formula was identified as $C_{21}H_{20}O_{11}$. Mass analysis result was $(M-H)^-$: 448 (m/z). H-NMR and C-NMR spectroscopy using the deuteromethanol solvent confirmed that the active compound was one having an antiviral activity [FIG. 2].

<NMR Data>
1) Compound represented by the formula (1)
$^{13}C$ NMR (MeOH-$d_6$) δ17.2, 23.1, 29.5, 30.3, 36.5, 39.2, 40.5, 79.7, 116.8, 121.0, 125, 137.8, 141.8, 149.1, 165.0.

EXAMPLE 3

Anti Coronaviral Activity of Quercetin-7-rhamnoside

In order to measure the anti-coronavirus activity of quercetin-7-rhamnoside, the present inventors performed the following in vitro test using Vero cells from the Vero cell line derived from kidney cells of African green monkey.

Inhibitory activity of quercetin-7-rhamnoside against viral proliferation was measured by the method proposed by Kwon Dur-Han, et al. (Korean Patent Application No. 2004-101863). Inhibitory activity against porcine epidemic diarrhea virus (PEDV), a kind of coronavirus, was measured. Vero cells were cultured on a 96-well microplate until the bottom of each well was completely covered with cells. Remaining culture medium was completely removed and each well was washed twice with a phosphate buffer. PEDV solution adjusted to a concentration of TCID50 was added to each well. Each of quercetin-7-rhamnoside; conventional antiviral agents purchased from Sigma-ribavirin, acyclovir, amantadine and azidothymidine; oseltamivir (trade name: Tamiflu) purchased from Roche; and zanamivir (trade name: Relenza) purchased from Glaxo Wellcome; dissolved in dimethyl sulfoxide was added to each well to a final concentration of 0.1-100 μg/mL. After culturing for 48 hours, the Vero cells were observed with a microscope. After adding 100 μL of 70% acetone, each well was kept at −20° C. for 1 hour. After drying in a desiccator, 100 μL of 0.4% (w/v) SRB (sulforhodamine B) solution dissolved in 1% (v/v) acetic acid was added. After 30 minutes' staining, the SRB staining solution not bound to the cells was washed off with 1% (v/v) acetic acid for 4 times.

After drying, 100 μL of 10 mM Tris solution (pH 10.5) was added to each well to dissolve the stained substance at the bottom of the well. Light absorbance was measured at 562 nm to evaluate the antiviral activity.

Cells treated with DMSO only and those treated with DMSO and PEDV was used as control groups. The antiviral activity against PEDV of the compound of the present invention is given in Table 1 below.

TABLE 1

Antiviral activity against PEDV in Vero cells

| Compounds | Inhibitory activity (TI = $CC_{50}/IC_{50}$) |
|---|---|
| Quercetin-7-rhamnoside | >7,143 [$CC_{50}/IC_{50}$ => (100 μg/mL)/ (0.014 μg/mL)] |
| Ribavirin | >24.4 [$CC_{50}/IC_{50}$ => (100 μg/mL)/ (4.1 μg/mL)] |
| Lamivudine | $IC_{50}$ not attained even at the maximum dosage |
| Azidothymidine | $IC_{50}$ not attained even at the maximum dosage |
| Acycloguanine | $IC_{50}$ not attained even at the maximum dosage |
| Tamiflu | $IC_{50}$ not attained even at the maximum dosage |
| Relenza | $IC_{50}$ not attained even at the maximum dosage |

As shown in Table 1, the antiviral inhibition index (TI=$CC_{50}/IC_{50}$; $CC_{50}$=the concentration required for 50% cytotoxicity, $IC_{50}$=the concentration required for 50% inhibition of viruses) of quercetin-7-rhamnoside was over 7,143. Quercetin-7-rhamnoside was superior in inhibiting viruses than the reference substance ribavirin (TI=244). Other antiviral agents, lamivudine, azidothymidine and acycloguanine, did not reach $IC_{50}$ even at the maximum dosage (100 μg/mL). Accordingly, it was confirmed that the compound quercetin-7-rhamnoside of the present invention is effective in inhibiting porcine epidemic diarrhea viruses in vitro.

The inhibitory activity index (>7,143) of quercetin-7-rhamnoside is more than 700 times higher than that of the methanol extract of Houttuynia cordata (10.1), which was filed patent application by Kwon Dur-Han, et al. [Korean Patent Application No. 2004-97587].

Inhibitory activity of quercetin-7-rhamnoside against PEDV was compared with other flavonoids having similar structures. Each of apigenin, luteolin, quercetin, catechin, quercitrin, genistin, hesperidin and rutin purchased from Sigma was dissolved in dimethyl sulfoxide and antiviral activity was measured at a concentration of 0.1-100 μg/mL. The result is given in Table 2 below.

TABLE 2

Antiviral Inhibitory activity of quercetin-7-rhamnoside and similar compounds

| Compounds | Inhibitory activity (TI = $CC_{50}/IC_{50}$) |
|---|---|
| Quercetin-7-rhamnoside | >7,143 [$CC_{50}/IC_{50}$ => (100 μg/mL)/ (0.014 μg/mL)] |
| Apigenin | >370 [$CC_{50}/IC_{50}$ => (50 μg/mL)/(0.1 μg/mL)] |
| Luteolin | >32.7 [$CC_{50}/IC_{50}$ => (6.7 μg/mL)/ (0.21 μg/mL)] |
| Quercetin | 34.2 [$CC_{50}/IC_{50}$ => (365.2 μg/mL)/ (10.7 μg/mL)] |
| Catechin | >9.0 [$CC_{50}/IC_{50}$ => (100 μg/mL)/(11.1 μg/mL)] |
| Quercitrin | $IC_{50}$ not attained even at the maximum dosage. |
| Genistin | $IC_{50}$ not attained even at the maximum dosage. |

TABLE 2-continued

Antiviral Inhibitory activity of quercetin-7-rhamnoside and similar compounds

| Compounds | Inhibitory activity (TI = $CC_{50}/IC_{50}$) |
|---|---|
| Hesperidin | $IC_{50}$ not attained even at the maximum dosage. |
| Rutin | $IC_{50}$ not attained even at the maximum dosage. |

Apigenin, luteolin and quercetin are compounds wherein sugars are not bound to flavonoid. Catechin is also a compound having a structure very similar to that of flavonoid but with no sugar. Genistin is a compound in which the No. 7 carbon of flavonoid is bound to glucose [see the formula (1)], hesperidin and rutin are compounds in which the No. 7 carbon of flavonoid is bound to two sugars (see the formula (1)) and quercitrin is a compound in which the No. 3 carbon of flavonoid is bound to rhamnose (see the formula (1)). As shown in Table 2, the antiviral inhibitory activity index (TI=$CC_{50}$/ $IC_{50}$) of apigenin was 370 and those of luteolin and quercetin were 32.7 and 34.2, respectively. The antiviral inhibitory activity index of catechin was 9.0 and quercitrin, genistin, hesperidin and rutin did not reach IC even at the maximum dosage (100 μg/mL). Accordingly, it was confirmed that the compound quercetin-7-rhamnoside of the present invention is superior in specifically inhibiting viruses in vitro, compared with similar flavonoids.

Antiviral activity of quercetin-7-rhamnoside against porcine transmissible gastroenteritis virus (TGEV) and porcine respiratory coronavirus (PRCV), another kind of coronaviruses, was evaluated. ST cells were cultured on a 96-well microplate until the bottom of each well was completely covered with cells. Remaining culture medium was completely removed and each well was washed twice with a phosphate buffer. TGEV or PRCV solution adjusted to a concentration of TCID50 was added to each well. Each of quercetin-7-rhamnoside, conventional antiviral agents purchased from Sigma-ribavirin, lamivudine, azidovudine, acycloguanine and glycyrrhizin-dissolved in dimethyl sulfoxide was added to each well to a final concentration of 0.1-100 μg/mL. After culturing for 48 hours, the ST cells were observed with a microscope. Similarly to the aforesaid evaluation of antiviral inhibitory activity against PEDV, c ells treated with DMSO only and those treated with both DMSO and TGEV or both DMSO and PRCV were used as control groups.

The antiviral activity against PEDV of the compound of the present invention is given in Table 1 below.

Lamivudine, azidovudine, acycloguanine and glycyrrhizin showed no inhibitory activity against TGEV and PRCV at all. Antiviral inhibitory activity of quercetin-7-rhamnoside and ribavirin is given in Table 3 below.

TABLE 3

Anti-coronavirus inhibitory activity in ST cells

| Viruses | Compounds | Inhibitory activity (TI = $CC_{50}/IC_{50}$) |
|---|---|---|
| TGEV | Quercetin-7-rhamnoside | >1.58 [$CC_{50}/IC_{50}$ => (100 μg/mL)/ (63.3 μg/mL)] |
|  | Ribavirin | >1.63 [$CC_{50}/IC_{50}$ => (100 μg/mL)/ (55.1 μg/mL)] |
| PRCV | Quercetin-7-rhamnoside | >1.67 [$CC_{50}/IC_{50}$ => (100 μg/mL)/ (59.8 μg/mL)] |
|  | Ribavirin | >1.62 [$CC_{50}/IC_{50}$ => (100 μg/mL)/ (61.6 μg/mL)] |

As shown in Table 3, quercetin-7-rhamnoside showed superior antiviral inhibitory activity against TGEV and PRCV comparable to that of ribavirin. In conclusion, quercetin-7-rhamnoside is effective in inhibiting the three types of coronaviruses-porcine epidemic diarrhea virus, porcine epidemic diarrhea viruses and porcine transmissible gastroentritis virus—in vitro.

EXAMPLE 4

Inhibitory Activity of Quercetin-7-rhamnoside Against Influenza Virus

In order to evaluate the inhibitory activity of quercetin-7-rhamnoside against influenza virus, the following in vitro test was performed using MDCK cells derived from dog kidney.

Inhibitory activity of quercetin-7-rhamnoside against viral proliferation was measured by the method proposed by Kwon Dur-Han, et al. (Korean Patent Application No. 2004-101863). Inhibitory activity against influenza virus type A (H1N1; WS/33 strain) was measured. MDCK cells were cultured on a 96-well microplate until the bottom of each well was completely covered with cells. Remaining culture medium was completely removed and each well was washed twice with a phosphate buffer. Each of quercetin-7-rhamnoside; conventional antiviral agents purchased from Sigma-ribavirin and amantadine; oseltamivir (trade name: Tamiflu) purchased from Roche; and zanamivir (trade name: Relenza) purchased from Glaxo Wellcome; dissolved in dimethyl sulfoxide was added to each well to a final concentration of 10 μg/mL. After culturing for 48 hours, the MDCK cells were observed with a microscope. After adding 100 μL of 70% acetone, each well was kept at −20° C. for 1 hour. After drying in a desiccator, 100 μL of 0.4% (w/v) SRB (sulforhodamine B) solution dissolved in 1% (v/v) acetic acid was added. After 30 minutes' staining, the SRB staining solution not bound to the cells was washed off with 1% (v/v) acetic acid for 4 times. After drying, 100 μL of 10 mM Tris solution (pH 10.5) was added to each well to dissolve the stained substance at the bottom of the well. Light absorbance was measured at 562 nm to evaluate the antiviral activity. As control group, viability of cells treated with DMSO only was compared with those treated with both DMSO and virus. Each test was repeated 3 times. Antiviral activity of each compound at a given concentration (10 μg/mL) is given in Table 4 below.

TABLE 4

Antiviral activity against influenza type A (H1N1/WS/33) virus

| Compounds (10 μg/mL) | Inhibitory activity (%) (Mean ± S.D.) |
|---|---|
| Quercetin-7-rhamnoside | 66.03 ± 4.85 |
| Ribavirin | 74.15 ± 4.01 |
| Relenza | 52.68 ± 0.29 |
| Tamiflu | −9.78 ± 0.67 |
| Amantadine | 14.60 ± 6.05 |

As shown in Table 4, quercetin-7-rhamnoside showed an inhibitory activity against influenza A virus in infected MDCK cells of 66.03%, which is significantly superior to that of Tamiflu (−9.78%), an agent currently used to treat the infection by influenza virus. It also showed superior inhibitory activity to Relenza (52.68%), which is used only for inhalation because of the high risk of side effects, and although amantadine (14.60%), which has been used to treat flu until 2000 but is hardly used currently because of side effects. Ribavirin (74.15%) showed superior inhibitory activity to quercetin-7-rhamnoside, but it is not used to treat flu because of the high risk of side effects such as anemia. To conclude, quercetin-7-rhamnoside of the present invention is a compound derived from natural product effective in inhibiting influenza virus in vitro.

EXAMPLE 5

Inhibitory Activity of Quercetin-7-rhamnoside Against Influenza Type B Virus

In order to evaluate the inhibitory activity of quercetin-7-rhamnoside against influenza virus, the following in vitro test was performed using MDCK cells derived from dog kidney.

Inhibitory activity of quercetin-7-rhamnoside against viral proliferation was measured by the method proposed by Kwon Dur-Han, et al. (Korean Patent Publication No. 2004-101863). Inhibitory activity against influenza type B (B/Lee/40) virus was measured. MDCK cells were cultured on a 96-well microplate until the bottom of each well was completely covered with cells. Remaining culture medium was removed and each well was washed twice with a phosphate buffer. An influenza virus solution adjusted to a concentration of TCID 50 was added to each well. Then, each of the compound of the present invention and conventional antiviral agents ribavirin and amantadine purchased from Sigma, oseltamivir (trade name: Tamiflu) purchased from Roche and zanavimir (trade name: Relenza) purchased from Glaxo Wellcome dissolved in dimethyl sulfoxide was added to each well at a concentration of 10 μg/mL. After 48 hours, the MDCK cells were observed with a microscope. After adding 100 μL of 70% acetone, each well was kept at −20° C. for 1 hour. After drying in a desiccator, 100 μL of 0.4% (w/v) SRB (sulforhodamine B) solution dissolved in 1% (v/v) acetic acid was added. After 30 minutes of staining, the SRB solution not bound to the cells was washed off with 1% (v/v) acetic acid for 4 times. After drying, 100 μL of 10 mM Tris solution (pH 10.5) was added to each well to dissolve the stained substance at the bottom of the well. Light absorbance was measured at 562 nm to evaluate the antiviral activity. As control group, viability of cells treated with DMSO only was compared with those treated with both DMSO and virus. Each test was repeated for 3 times. Antiviral activity of each compound at a given concentration (10 μg/mL) is given in Table 5 below.

TABLE 5

| Inhibitory activity against influenza type B (B/Lee/40) virus | |
|---|---|
| Compounds (10 μg/mL) | Inhibitory activity (%) (Mean ± S.D.) |
| Quercetin-7-rhamnoside | 92.66 ± 0.24 |
| Ribavirin | 95.77 ± 0.79 |
| Relenza | 3.40 ± 3.92 |
| Tamiflu | −1.43 ± 2.98 |
| Amantadine | −1.85 ± 1.66 |

As shown in Table 5, quercetin-7-rhamnoside showed an inhibitory activity against influenza B virus in infected MDCK cells of 92.66%, which is significantly superior to that of Tamiflu (−1.43%), which is currently used to treat the infection by influenza virus. It also showed superior inhibitory activity to Relenza (3.40%), which is used only for inhalation because of the high risk of side effects, and although amantadine (−1.85%), which had been used to treat flu until 2000 but is hardly used currently because of side effects. Ribavirin (95.77%) showed superior inhibitory activity to quercetin-7-rhamnoside, but it is not used to treat flu because of the high risk of side effects such as anemia. To conclude, quercetin-7-rhamnoside of the present invention is a compound derived from natural product effective in inhibiting influenza virus in vitro.

EXAMPLE 6

Inhibitory Activity of Quercetin-7-rhamnoside Against Rotavirus

In order to evaluate the inhibitory activity of quercetin-7-rhamnoside against rota virus, the following in vitro test was performed using MA014 cells derived from pig kidney.

Inhibitory activity of quercetin-7-rhamnoside against viral proliferation was measured by the method proposed by Kwon Dur-Han, et al. (Korean Patent Publication No. 2004-101863). Inhibitory activity against rotavirus (strain: OSU) was measured. MA104 cells were cultured on a 96-well microplate until the bottom of each well was completely covered with cells. Remaining culture medium was removed and each well was washed twice with a phosphate buffer. A rota virus solution adjusted to a concentration of TCID 50 was added to each well. Then, each of the compound of the present invention and conventional antiviral agents ribavirin, azidothymidine, acyclovir, lamivudine and glycyrrhizin purchased from Sigma and zanavimir (trade name: Relenza) purchased from Glaxo Wellcome dissolved in dimethyl sulfoxide was added to each well at a concentration of 10 μg/mL. After 48 hours, the MA104 cells were observed under a microscope. After adding 100 μL of 70% acetone, each well was kept at −20° C. for 1 hour. After drying in a desiccator, 100 μL of 0.4% (w/v) SRB (sulforhodamine B) solution dissolved in 1% (v/v) acetic acid was added. After 30 minutes of staining, the SRB solution not bound to the cells was washed off with 1% (v/v) acetic acid for 4 times. After drying, 100 μL of 10 mM Tris solution (pH 10.5) was added to each well to dissolve the stained substance at the bottom of the well. Light absorbance was measured at 562 nm to evaluate the antiviral activity. As control group, viability of cells treated with DMSO only was compared with those treated with both DMSO and virus. Each test was repeated for 2 times. Antiviral activity of each compound at a given concentration (10 μg/mL) is given in Table 6 below.

TABLE 6

| Inhibitory activity against rotavirus | |
|---|---|
| Compounds (10 μg/mL) | Inhibitory activity (%) (Mean ± S.D.) |
| Quercetin-7-rhamnoside | 77.37 ± 1.96 |
| Ribavirin | 82.34 ± 5.86 |
| Azidothymidine | 0.69 ± 0.75 |
| Acyclovir | 0.78 ± 0.81 |
| Lamivudine | 0.02 ± 0.12 |
| Glycyrrhizin | 0.49 ± 0.22 |
| Relenza | 0.50 ± 0.40 |

As shown in Table 6, quercetin-7-rhamnoside showed an inhibitory activity against rotavirus in infected MA104 cells of 77.37%, which is significantly superior to those of azidothymidine (0.69%), acyclovir (0.78%), lamivudine (0.02%) and Relenza (0.50%), which are currently used as anti viral agents. Whereas the inhibitory activity of glycyrrhizin, a natural product with antiviral activity, was only 0.49%, quercetin-7-rhamnoside showed an excellent inhibitory activity of 77.37%. Ribavirin (82.34%) showed superior inhibitory activity to quercetin-7-rhamnoside, but it is not used to treat flu because of the high risk of side effects such as anemia. To conclude, quercetin-7-rhamnoside of the present invention is a compound derived from natural product effective in inhibiting rotavirus in vitro.

EXAMPLE 7

Inhibitory Activity of Quercetin-7-rhamnoside Against Rhinovirus

In order to evaluate the inhibitory activity of quercetin-7-rhamnoside against rhino virus, the following in vitro test was performed using HeLa, one of human cervical cancer cell lines, cells.

Inhibitory activity of quercetin-7-rhamnoside against viral proliferation was measured by the method proposed by Kwon Dur-Han, et al. (Korean Patent Publication No. 2004-101863). Inhibitory activity against rhinovirus (strain: rhinovirus 2) was measured. HeLa cells were cultured on a 96-well microplate until the bottom of each well was completely covered with cells. Remaining culture medium was removed and each well was washed twice with a phosphate buffer. A rhino virus solution adjusted to a concentration of TCID 50 was added to each well. Then, each of the compound of the present invention and quercetin, luteolin, apigenin, quercitrin, genistin, hesperidin, catechin and lutin, which are flavonoid compounds similar to quercetin-7-rhamnoside, and a conventional antiviral agent ribavirin purchased from Sigma dissolved in dimethyl sulfoxide was added to each well at a concentration of 10 μg/mL. After 48 hours, the HeLa cells were observed under a microscope. After adding 100 μL of 70% acetone, each well was kept at −20° C. for 1 hour. After drying in a desiccator, 100 μL of 0.4% (w/v) SRB (sulforhodamine B) solution dissolved in 1% (v/v) acetic acid was added. After 30 minutes of staining, the SRB solution not bound to the cells was washed off with 1% (v/v) acetic acid for 4 times. After drying, 100 μL of 10 mM Tris solution (pH 10.5) was added to each well to dissolve the stained substance at the bottom of the well. Light absorbance was measured at 562 nm to evaluate the antiviral activity. As control group, viability of cells treated with DMSO only was compared with those treated with both DMSO and virus. Each test was repeated for 3 times. Antiviral activity of each compound at a given concentration (10 μg/mL) is given in Table 7 below.

TABLE 7

Inhibitory activity against rhinovirus

| Compounds (10 μg/mL) | Inhibitory activity (%) (Mean ± S.D.) |
|---|---|
| Quercetin-7-rhamnoside | 77.89 ± 1.18 |
| Quercetin | 9.87 ± 4.67 |
| Luteolin | 21.82 ± 1.82 |
| Apigenin | 9.24 ± 8.31 |
| Quercitrin | 13.43 ± 4.24 |
| Genistin | 12.97 ± 2.10 |
| Hesperidin | 3.12 ± 14.90 |
| Catechin | 11.21 ± 4.06 |
| Lutin | 25.68 ± 1.06 |
| Ribavirin | 42.32 ± 4.38 |

As shown in Table 7, whereas quercetin (9.87%), luteolin (21.82%), apigenin (9.24%), quercitrin (13.43%), genistin (12.97%), hesperidin (3.12%), lutin (25.68%) and catechin (11.21%), which are flavonoid compounds having similar structures to that of quercetin-7-rhamnoside, did not show superior inhibitory activity against rotavirus, quercetin-7-rhamnoside showed an excellent inhibitory activity of 77.89%. Ribavirin (42.342%), which is one of strong antiviral agents, showed worse inhibitory activity than quercetin-7-rhamnoside. Thus, it can be concluded that quercetin-7-rhamnoside of the present invention is a compound derived from natural product effective in inhibiting rhinovirus in vitro.

EXAMPLE 8

Toxicity Test

Toxicity test was performed as follows for the quercetin-7-rhamnoside of the present invention.

Quercetin-7-rhamnoside dissolved in dimethyl sulfoxide (DMSO) and diluted with water was administered to mice (10 per each group) at a dosage of 10 g/kg. The mice were observed for 7 days and none of them were found dead.

PREPARATION EXAMPLE 1

Powder

Active ingredient 10 g
Cornstarch 50 g
Carboxycellulose 40 g
Total 100 g

The above components were finely crushed and mixed to obtain powder. 100 mg of the resultant powder was filled in hard capsule No. 5.

PREPARATION EXAMPLE 2

Tablet

Active ingredient 10 g
Lactose 70 g
Crystalline cellulose 15 g
Magnesium stearate 5 g
Total 100 g The above components were finely crushed and mixed. Tablets were prepared by the direct tableting method. The total weight of each tablet was 100 mg and 10 mg of the active ingredient was contained in each tablet.

PREPARATION EXAMPLE 3

Injection

Active ingredient 10 mg
Sodium chloride 600 mg
Ascorbic acid 100 mg
Water for injection adequate
Total 100 mL An injection was prepared with the above components. The solution was filled in an ampule and heated at 120° C. for 30 minutes for sterilization.

INDUSTRIAL APPLICABILITY

As apparent from the foregoing description, the flavonoid compound in accordance with the present invention or a pharmaceutically acceptable salt thereof can be utilized to treat or prevent the diseases caused by viral infection.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method for the treatment of diarrhea caused by corona virus, dehydration caused by corona virus, flu or cold which comprises administering an effective amount of an antiviral composition, comprising an isolated flavonoid compound represented by the formula (1) or a pharmaceutically acceptable salt thereof as an active ingredient:

(1)

[Chemical structure of flavonoid with rhamnose-O at position 7, R1 at position 5, R2 at position 3, R3 and R4 on ring C]

wherein each of R1, R2, R3 and R4 is selected from H, OH or alkyl, to a patient in need thereof.

2. The method as set forth in claim 1, wherein the compound is represented by the following formula (1a):

(1a)

[Chemical structure with rhamnose-O, OH groups, and H]

3. The method as set forth in claim 2 wherein the treatment is for diarrhea caused by corona virus.

4. A method for extracting and isolating an active ingredient having an antiviral activity from *Houttuynia cordata*, comprising:
   1) extracting *Houttuynia cordata* with methanol, concentrating the extract under reduced pressure and extracting the same with ethyl acetate to obtain an ethyl acetate extract;
   2) concentrating the ethyl acetate extract and dissolving the concentrate in methanol and collecting an active fraction by silica gel column adsorption chromatography and column chromatography using a Sephadex LH-20 column; and
   3) separating the active fraction by high pressure liquid chromatography, removing the solvent using a vacuum dryer and freeze-drying the product to obtain a compound having an antiviral activity.

5. The method as set forth in claim 4, wherein the compound having an antiviral activity is a compound represented by the following formula (1):

(1)

[Chemical structure of flavonoid with rhamnose-O at position 7, R1 at position 5, R2 at position 3, R3 and R4 on ring C]

wherein each of R1, R2, R3 and R4 is selected from H, OH or alkyl.

6. The method as set forth in claim 2, wherein the treatment is for dehydration caused by corona virus.

7. The method as set forth in claim 2, wherein the treatment is for flu.

8. The method as set forth in claim 2, wherein the treatment is for cold.

* * * * *